US012135763B2

(12) United States Patent
Sawkey

(10) Patent No.: US 12,135,763 B2
(45) Date of Patent: Nov. 5, 2024

(54) AUTOMATIC LOCALIZED EVALUATION OF CONTOURS WITH VISUAL FEEDBACK

(71) Applicant: SIEMENS HEALTHINEERS INTERNATIONAL AG, Steinhausen (CH)

(72) Inventor: Daren Sawkey, Palo Alto, CA (US)

(73) Assignee: SIEMENS HEALTHINEERS INTERNATIONAL AG, Steinhausen (CH)

( * ) Notice: Subject to any disclaimer, the term of this patent is extended or adjusted under 35 U.S.C. 154(b) by 516 days.

(21) Appl. No.: 17/361,110

(22) Filed: Jun. 28, 2021

(65) Prior Publication Data
US 2022/0414402 A1 Dec. 29, 2022

(51) Int. Cl.
*G06F 18/21* (2023.01)
*G06F 18/214* (2023.01)
(Continued)

(52) U.S. Cl.
CPC .......... *G06F 18/217* (2023.01); *G06F 18/214* (2023.01); *G06N 3/045* (2023.01);
(Continued)

(58) Field of Classification Search
CPC ........ G16H 15/00; G16H 30/20; G16H 30/40; G16H 40/20; G16H 50/20; G06V 10/46;
(Continued)

(56) References Cited

U.S. PATENT DOCUMENTS 9,757,589 B2 9/2017 Zankowski
10,675,486 B2 6/2020 Toimela et al.
(Continued)

FOREIGN PATENT DOCUMENTS

WO WO-2023/278196 A1 1/2023

OTHER PUBLICATIONS

Amine Amyar et al: "Weakly Supervised PET Tumor Detection Using Class Response", arxiv.org, Cornell University Library, 201 Olin Library Cornell University Ithaca, NY 14853, Mar. 18, 2020 (Mar. 18, 2020), XP081624167, p. 4-p. 5; figure 2.
(Continued)

*Primary Examiner* — Manuchehr Rahmjoo
(74) *Attorney, Agent, or Firm* — FOLEY & LARDNER LLP

(57) ABSTRACT

A localized evaluation network incorporates a discriminator acting as classifier, which may be included within a generative adversarial network (GAN). GAN may include a generative network such as U-NET for creating segmentations. The localized evaluation network is trained on image pairs including medical images of organs of interest and segmentation (mask) images. The network is trained to distinguish whether an image pair does or does not represent the ground
(Continued)

truth. GAN examines interior layers of the discriminator and evaluates how much each localized image region contributes to the final classification. The discriminator may analyze regions of the image pair that contribute to a classification by analyzing layer weights of the machine learning model. Disclosed embodiments include a visual attribute, such as a heat map, that represents contributions of localized regions of a contour to an overall confidence score. These localized regions may be highlighted and reported for quality assurance review.

20 Claims, 4 Drawing Sheets

(51) Int. Cl.
G06N 3/045 (2023.01)
G06N 3/088 (2023.01)
G06T 7/11 (2017.01)
G06T 7/12 (2017.01)
G06T 11/20 (2006.01)
G06V 10/46 (2022.01)
G16H 30/20 (2018.01)
G16H 30/40 (2018.01)
G16H 50/20 (2018.01)
G16H 15/00 (2018.01)
G16H 40/20 (2018.01)

(52) U.S. Cl.
CPC ............ G06N 3/088 (2013.01); G06T 7/11 (2017.01); G06T 7/12 (2017.01); G06T 11/203 (2013.01); G06V 10/46 (2022.01); G16H 30/20 (2018.01); G16H 30/40 (2018.01); G16H 50/20 (2018.01); G06T 2200/24 (2013.01); G06T 2207/10081 (2013.01); G06T 2207/10088 (2013.01); G06T 2207/10104 (2013.01); G06T 2207/20081 (2013.01); G06T 2207/20084 (2013.01); G06T 2207/30004 (2013.01); G06V 2201/031 (2022.01); G16H 15/00 (2018.01); G16H 40/20 (2018.01)

(58) Field of Classification Search
CPC .. G06V 10/752; G06V 10/774; G06V 10/778; G06V 10/82; G06V 2201/031; G06T 11/203; G06T 2200/24; G06T 2207/10072; G06T 2207/10081; G06T 2207/10088; G06T 2207/10104; G06T 2207/10116; G06T 2207/20081; G06T 2207/20084; G06T 2207/20104; G06T 2207/30004; G06T 2207/30016; G06T 2207/30096; G06T 2207/30168; G06T 7/0012; G06T 7/11; G06T 7/12; G06N 3/045; G06N 3/088; G06F 18/214; G06F 18/217
See application file for complete search history.

(56) References Cited

U.S. PATENT DOCUMENTS

| | | | |
|---|---|---|---|
| 10,936,912 B2 | 3/2021 | Nakano et al. | |
| 10,967,202 B2 | 4/2021 | Van Heteren et al. | |
| 11,049,044 B1* | 6/2021 | Habenschuss | G06N 3/08 |
| 11,282,291 B1* | 3/2022 | Boardman | G06T 1/0007 |
| 2012/0027271 A1 | 2/2012 | Zankowski | |
| 2019/0259153 A1 | 8/2019 | Zhang et al. | |
| 2020/0201971 A1* | 6/2020 | Wei | G06N 3/08 |
| 2020/0202533 A1* | 6/2020 | Cohen | G06T 7/194 |
| 2021/0177373 A1* | 6/2021 | Xie | G06N 3/04 |
| 2021/0272284 A1* | 9/2021 | Kamiyama | G16H 50/70 |
| 2023/0320698 A1* | 10/2023 | Takeda | A61B 8/085 |
| | | | 600/437 |

OTHER PUBLICATIONS

Bolei Zhou et al: "Learning Deep Features for Discriminative Localization", Dec. 14, 2015 (Dec. 14, 2015), XP055370526, DOI: 10.1109/CVPR.2016.319 Retrieved from the Internet: URL:https:// arxiv.org/pdf/1512.04150.pdf [retrieved on May 9, 2017] cited in the application abstract p. 2-p. 3; figures 2,3.

International Search Report and Written Opinion on PCT Appl. Ser. No. PCT/US2022/034253 dated Oct. 17, 2022 (17 pages).

Kang Hanul et al: "Towards a quantitative analysis of class activation mapping for deep learning-based computer-aided diagnosis", Progress in Biomedical Optics and Imaging?? SPIE—International Society for Optical Engineering, Bellingham, WA, US, vol. 11599, Feb. 15, 2021 (Feb. 15, 2021), pp. 115990M-115990M, XP060139962, ISSN: 1605-7422, DOI: 10.1117/12.2580819 ISBN: 978-1-5106-0027-0 abstract p. 5-p. 6; figure 2.

Selvaraju Ramprasaath R et al: "Grad-CAM: Visual Explanations from Deep Networks via Gradient-Based Localization", arxiv.org, Cornell University Library, 201 Olin Library Cornell University Ithaca, NY 14853, vol. 128, No. 2, Oct. 11, 2019 (Oct. 11, 2019), pp. 336-359, XP037015152, DOI: 10.1007/S11263-019-01228-7 [retrieved on Oct. 11, 2019] cited in the application abstract p. 3-p. 4; figure 2.

Brie Goo, Katrina May, Haobo Zhang, James Olivas; "Machine Learning Solution to Organ-At-Risk Segmentation for Radiation Treatment Planning;" Santa Clara University, Interdisciplinary Design Senior Theses; Jun. 13, 2019; 41 pages.

Carlos E Cardenas, Jinzhong Yang, Brian M Anderson, Laurence E Court, Kristy B Brock; "Advances in Auto-Segmentation;" Semin Radiat Oncol. Jul. 2019:185-197; Jul. 2019, 13 pages.

Chenjie Ge, Irene Yu-Hua Gu, Asgeir Store Jakola, Jie Yang; "Deep semi-supervised learning for brain tumor classification"; BMC Medical Imaging vol. 20; Jul. 29, 2020; 11 pages.

Edgar Schonfeld, Bernt Schiele, Anna Khoreva; A U-Net Based Discriminator for Generative Adversarial Networks; CVPR 2020 (Main Conference); Feb. 28, 2020; 10 pages.

Ehsan Adeli; Kim-Han Thung; Le An; Guorong Wu; Feng Shi; Tao Wang; Dinggang Shen; "Semi-Supervised Discriminative Classification Robust to Sample-Outliers and Feature-Noises;" IEEE Transactions on Pattern Analysis and Machine Intelligence, vol. 41, Issue 2; Feb. 1, 2019; 8 pages.

Elias H. Cohen; ManishSingh; "Geometric determinants of shape segmentation: Tests using segment identification;" Vision Research, vol. 47, Issue 22, pp. 2825-2840; Oct. 2007; 16 pages.

F. Vaassen, C. Hazelaar, A. Vaniqui, M. Gooding, B. van der Heyden, R. Canters, W. V. van Elmpt; "Evaluation of measures for assessing time-saving of automatic organ-at-risk segmentation in radiotherapy;" Physics and Imaging in Radiation Oncology, vol. 13, pp. 1-6; Jan. 2020; 6 pages.

Francois Chollet; "Grad-CAM class activation visualization"; https:// keras.io/examples/vision/grad_cam/; Apr. 26, 2020; 5 pages.

Gregory Sharp, Karl D Fritscher, Vladimir Pekar, Marta Peroni, Nadya Shusharina, Harini Veeraraghavan, Jinzhong Yang; "Vision 20-20_Perspectives on automated image segmentation for radiotherapy;" published online Med Phys. May 2014; 41(5): 050902; Apr. 24, 2014; 13 pages.

Haradhan Chel, P K Bora; "Novel Outlier Detection Based Approach to Registering Pre- and Post-resection Ultrasound Brain Tumor Images;" 2017 4th International Conference on Advances in Electrical Engineering (ICAEE); Sep. 2017; 7 pages.

Luca Biasiolli, Qiang Zhang, Iulia A. Popescu, Konrad Werys, Elena Lukaschuk, Valentina Carapella, Jose M. Paiva, Nay Aung, Jennifer J. Rayner, Kenneth Fung, Henrike Puchta. Mihir M. Sanghvi, Niall O. Moon, Katharine E. Thomas; "Quality Control-Driven Image Segmentation Towards Reliable Automatic Image

(56) References Cited

OTHER PUBLICATIONS

Analysis in Large-Scale Cardiovascular Magnetic Resonance Aortic Cine Imaging;" Lecture Notes in Computer Science (LNCS, vol. 11765); Oct. 10, 2019; 9 pages.

Object Category Classification Using Occluding Contours; 6th International Symposium, ISVC 2010, Las Vegas, NV, USA, Nov. 29-Dec. 1, 2010.10 pages.

Rajkumar Theagarajan, Bir Bhanu,; "DeephESC 2.0: Deep Generative Multi Adversarial Networks for improving the classification of hESC;" PloS one, 14(3); Mar. 6, 2019; 29 pages.

Ramprasaath R. Selvaraju, Michael Cogswell, Abhishek Das, Ramakrishna Vedantam, Devi Parikh, Dhruv Batra; "Grad-CAM: Visual Explanations from Deep Networks via Gradient-based Localization," 2017 IEEE International Conference on Computer Vision; Oct. 22-29, 2017; 9 pages.

Xiaocong Chen, Yun Li, Lina Yao, Ehsan Adeli, Yu Zhang; "Generative Adversarial U-Net for Domain-free Medical Image Augmentation;" arXiv:2101.04793; Jan. 12, 2021; 7 pages.

GitHub—phillipi/pix2pix: Image-to-image translation with conditional adversarial nets.

Head-Neck-PET-CT, Cancer Imaging Archive, Jun. 7, 2018 (4 pages).

* cited by examiner

400

Execute a machine learning model that receives an input of a first image of an anatomical region of a patient depicting an organ having an outline and a second image comprising an overlay contouring the outline and configured to predict a first confidence score indicating a likelihood of the overlay correctly contouring the outline, wherein the machine learning model is trained based on a set of third images depicting a set of second organs having a set of second outlines and a set of fourth images including a set of second overlays incorrectly contouring the set of second outlines. 402

Present, for display on a graphical user interface, the first image and a third overlay, wherein a plurality of localized regions within the third overlay have a visual attribute that represents contributions of respective localized regions to the first confidence score 404

FIG. 4

AUTOMATIC LOCALIZED EVALUATION OF CONTOURS WITH VISUAL FEEDBACK

TECHNICAL FIELD

This application relates generally to artificial intelligence modeling for localized quality assurance evaluation of organ segmentations.

BACKGROUND

Radiotherapy (radiation-based therapy) is used as a cancer treatment to emit high doses of radiation that can kill cells or shrink a tumor. The goal is to deliver enough radiation to a target region of the patient's anatomy to kill the cancerous cells during the radiotherapy treatment. Other organs or anatomical regions that are adjacent to, or surrounding, the target region can be in the way of radiation beams and can receive enough radiation to damage or harm such organs. A physician or a radiation oncologist identifies organs of interest, which would typically include both the target region and the organs at risk, prior to radiotherapy using various imaging modalities. Furthermore, simulation images of the patient's anatomy may be obtained.

For safe and effective radiotherapy treatment, it is crucial to accurately segment organs of interest. Manual delineation of target volumes and organs at risk is still standard routine for many clinics, even though it is time consuming and prone to intra-observer and inter-observer variations. Automated segmentation methods seek to reduce delineation workload and unify the organ boundary definition. In deploying automated segmentation to clinical applications, however, it is necessary to address the issue of quality control. State-of-the-art autosegmentation methods such as methods incorporating machine learning can still fail. Additionally, existing methods do not lend themselves to fully automated contouring. It is important to detect any critical inaccuracies, which can lead to misidentification.

Current clinical practice of segmentation quality control requires human visual inspection, e.g., by a radiation oncologist. Autosegmentation algorithms do not provide any guidance to the user as to which regions of the segmentation results should be evaluated closely. Therefore a clinician providing second check to the segmentation algorithm needs to evaluate every region of every contour. This is very resource intensive. This poses a need for automated techniques that can highlight regions of the contours, most likely to need correcting, for a human to evaluate.

SUMMARY

For the aforementioned reasons, there is a need for systems and methods for automatic localized evaluation of contours of organs of interest to highlight problematic regions of the contours for a human to evaluate. There is a need for automatic evaluation of segmentation of an organ of interest that provides a confidence level for the organ segmentation. Disclosed systems and methods for quality assurance identify regions of a contour that contribute to a low confidence level of an organ segmentation. Disclosed systems and methods automatically evaluate organ contours to provide visual indications of confidence level of localized areas of the contours.

As described in embodiments herein, a dual-input machine learning neural network classifier may be trained on image pairs including medical images of organs of interest and segmentation (mask) images. These image pairs are of two types: image pairs in which the mask image is the ground truth segmentation, and image pairs in which the mask differs from the ground truth. The machine learning classifier is trained to distinguish whether an image pair represents the ground truth, or does not represent the ground truth. Training data may incorporate two data sets. One data set includes medical images of organs of interest plus ground truth segmentation (mask) images. The other data set includes medical images of organs of interest plus segmentation (mask) images that differ from the ground truth. The neural network classifier is trained to distinguish between the two data sets.

After training, when presented with a medical image/mask pair, the neural network classifies the medical image/mask pair as representing the ground truth or not. If the image pair is classified as not representing ground truth, the network may determine localized regions of the medical image/mask pair that contribute to the classification by analyzing layer weights of the neural network. These localized regions may be highlighted and reported to a clinician for quality assurance review.

A localized evaluation network may incorporate a discriminative network, also referred to herein as discriminator, which acts as a classifier. The localized evaluation network may include a generative network, also referred to as a generator. In an embodiment, the discriminative and generative networks collectively form a Generative Adversarial Network (GAN). In an embodiment, the generative network may be a Convolutional Neural Network (CNN), such as U-Net, configured to generate segmentations.

The localized evaluation network may apply the GAN to determine weights of interior layers of the discriminator. In an embodiment, a Class Activation Map (CAM) may examine the interior layers and evaluate how much each localized image region contributes to the final classification. Disclosed embodiments provide visual indications of confidence level of localized regions of the contours, e.g., via a heat map.

In an embodiment, a method comprises executing, by a processor, a machine learning model that receives an input of a first image of an anatomical region of a patient depicting an organ having an outline and a second image comprising an overlay contouring the outline and further configured to predict a first confidence score indicating a likelihood of the overlay matching the outline, wherein the machine learning model is trained based on a set of third images depicting a set of second organs having a set of second outlines and a set of fourth images comprising a set of second overlays incorrectly contouring the set of second outlines; and presenting, by the processor for display on a graphical user interface, the first image and a third overlay, wherein a plurality of localized regions within the third overlay have a visual attribute that represents contributions of respective localized regions of the plurality of localized regions to the first confidence score.

The overlay within the second image may be generated via a second machine learning model.

The set of fourth images may be previously generated via the second machine learning model.

The method may further comprise training the machine learning model based on a set of fifth images depicting a set of third organs having a set of third outlines and a set of sixth images comprising a set of fourth overlays correctly contouring the set of third outlines.

The first confidence score may indicate a likelihood of a plurality of localized regions of the overlay correctly contouring localized regions of the outline. The first confidence score may indicate likelihood that the relation between the overlay and the anatomical image is similar to those in the training data that are labelled as correct.

The machine learning model may be trained by applying a GAN to training data from the set of third images and the set of fourth images.

The machine learning model may be trained by applying the GAN to determine weights of interior layers of a discriminator.

The discriminator may generate a CAM to determine image regions that result in a reduced confidence score based on training data from the set of third images and the set of fourth images.

The contributions of the respective localized regions to the first confidence score may correspond to weights of layers of the machine learning model.

The visual attribute may correspond to color coding of a spatial heat map.

The machine learning model may be trained via a supervised training protocol.

The machine learning model may be a binary classifier with matched and unmatched classes.

The first image may be a computed tomography (CT) image, magnetic resonance imaging (MRI) image, or positron emission tomography (PET) scan image.

In an embodiment, a system comprises a server comprising a processor and a non-transitory computer-readable medium containing instructions that when executed by the processor causes the processor to perform operations comprising: executing a machine learning model that receives an input of a first image of an anatomical region of a patient depicting an organ having an outline and a second image comprising an overlay contouring the outline and further configured to predict a first confidence score indicating a likelihood of the overlay matching the outline, wherein the machine learning model is trained based on a set of third images depicting a set of second organs having a set of second outlines and a set of fourth images comprising a set of second overlays incorrectly contouring the set of second outlines; and present, for display on a graphical user interface, the first image and a third overlay, wherein a plurality of localized regions within the third overlay have a visual attribute that represents contributions of respective localized regions of the plurality of localized regions to the first confidence score.

The instructions when executed by the processor may cause the processor to train the machine learning model by applying a GAN to training data from the set of third images and the set of fourth images.

The machine learning model may be trained by applying the GAN to determine weights of interior layers of a discriminator.

The discriminator may generate a CAM to determine image regions that result in a reduced confidence score based on training data from the set of third images and the set of fourth images.

The CAM may comprise a Gradient-weighted Class Activation Map (Grad-CAM).

The visual attribute may correspond to color coding of a spatial heat map.

The machine learning model may be further trained based on a set of fifth images depicting a set of third organs having a set of third outlines and a set of sixth images comprising a set of fourth overlays correctly contouring the set of third outlines

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIG. 4 illustrates a flow diagram of a process for automated localized evaluation of contours, according to an embodiment.

DETAILED DESCRIPTION

Figure 1:
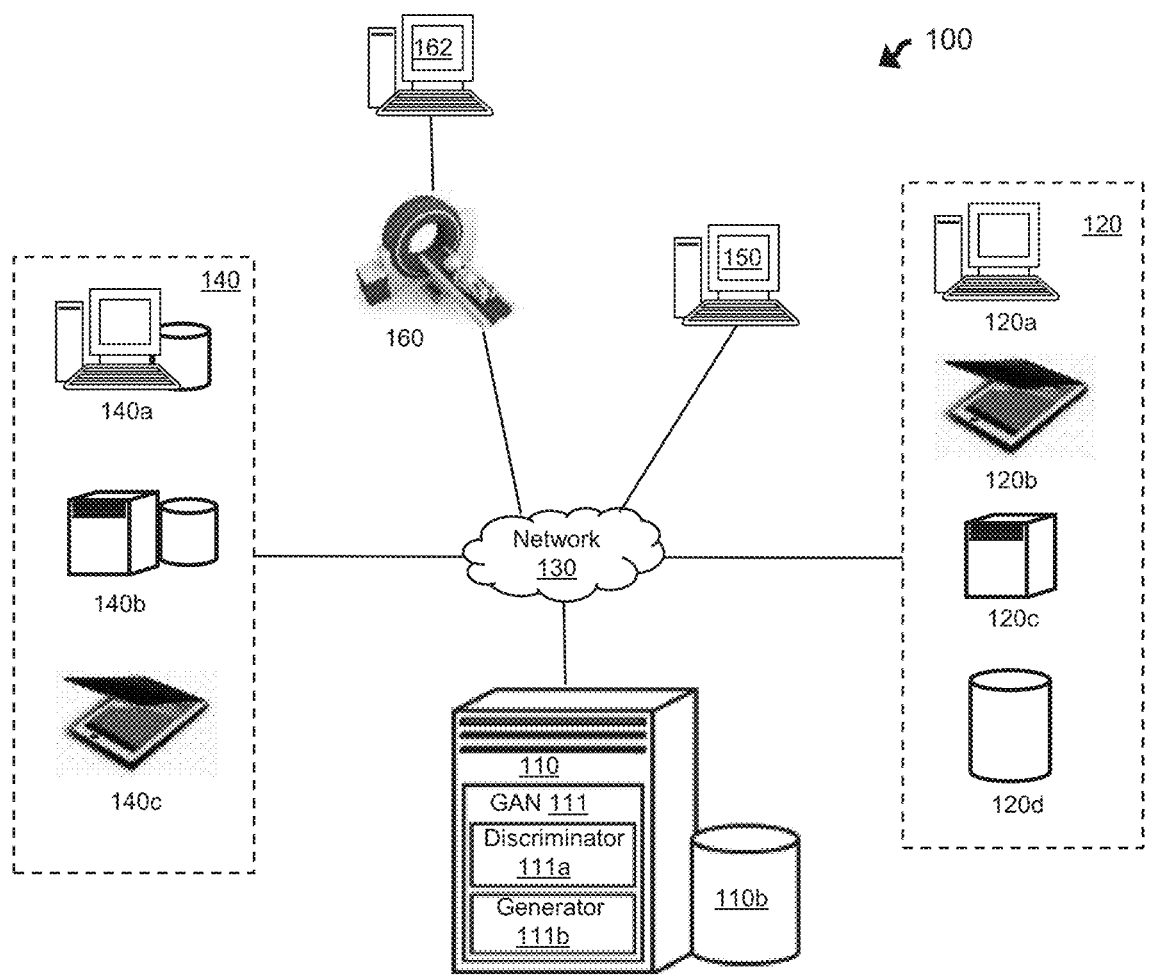
FIG. 1 illustrates components of a system for automated localized evaluation of contours, according to an embodiment.

Reference will now be made to the illustrative embodiments depicted in the drawings, and specific language will be used here to describe the same. It will nevertheless be understood that no limitation of the scope of the claims or this disclosure is thereby intended. Alterations and further modifications of the inventive features illustrated herein, and additional applications of the principles of the subject matter illustrated herein, which would occur to one skilled in the relevant art and having possession of this disclosure, are to be considered within the scope of the subject matter disclosed herein. Other embodiments may be used and/or other changes may be made without departing from the spirit or scope of the present disclosure. The illustrative embodiments described in the detailed description are not meant to be limiting of the subject matter presented.

When medical imaging is necessary to observe an internal organ or a set of internal organs, there are several systems that may be utilized such as X-ray, computed tomography (CT), cone beam CT images (CBCT), four-dimensional CT images (e.g., CT images over time), magnetic resonance imaging (MRI) images, positron emission tomography (PET) images, ultrasound images, and or a combination thereof. Medical images may be two-dimensional or three-dimensional (volumetric). A two-dimensional medical image may be a cross-sectional "slice" of a three-dimensional volume.

One purpose of three-dimensional reconstruction of the structure(s) of interest containing diseased or abnormal tissues or organs is the preparation of a three-dimensional radiation therapy treatment plan. To verify that a radiation treatment procedure is correctly applied, quality assurance protocols are implemented to verify that the developed treatment plan is accurate.

Radiation therapy treatment plans are used during medical procedures that selectively expose precise areas of the body, such as cancerous tumors, to specific doses of radiation to destroy the undesirable tissues. An initial treatment plan may be prepared that defines the area in the human body to be treated, such as cancerous tissue, abnormal cells, lesions, and organs, called the clinical target volume (CTV). Another volume called the planning target volume (PTV) allows for uncertainties in planning or treatment delivery to ensure that the radiotherapy dose is actually delivered to the CTV. Radiotherapy planning generally considers critical normal tissue structures near the CTV, known as organs at risk (OARs). The goal is to deliver enough radiation to the PTV to kill the cancerous cells during the radiotherapy treatment. OARs that are adjacent to, or surrounding, the PTV can be in the way of radiation beams and can receive enough radiation to damage or harm such organs or anatomical regions. Typically a physician or a radiation oncologist identifies both the PTV and the OARs prior to radiotherapy using a suitable imaging modality. Additionally, a physician or radiation oncologist may identify lesions, e.g., regions in an organ or tissue that have suffered damage through injury or disease. Furthermore, simulation images of the patient's anatomy may be obtained. PTV, OARs, lesions and other organs or anatomical regions of interest to a physician or a radiation oncologist in planning radiotherapy are referred to herein as organs of interest.

For safe and effective radiotherapy treatment, it may be crucial to accurately segment organs of interest. Manual segmentation methods require significant amounts of specialist time, while automated segmentation methods may be deployed to reduce delineation workload. In contouring organs of interest in clinical applications it is necessary to address the issue of quality control. State-of-the-art autosegmentation methods such as methods incorporating machine learning can still fail. Autosegmentation algorithms typically do not provide any guidance to the user as to which regions of the segmentation results should be evaluated closely. Clinicians providing second check to the segmentation algorithm need to evaluate every region of every contour which is very resource intensive.

Embodiments disclosed herein integrate automatic localized evaluation of contours of organs of interest to highlight problematic regions of the contours for a human to evaluate. Automatic evaluation of segmentation of an organ of interest may provide a confidence level for the organ segmentation. Systems and methods for quality assurance identify regions of a contour that contribute to a low confidence level of an organ segmentation. Embodiments disclosed herein automatically evaluate contours and provide visual indications of confidence level of localized regions of the contours.

FIG. 1 illustrates components of a system for automated localized evaluation of contours 100, according to an embodiment. The system 100 may include an analytics server 110a, system database 110b, machine learning models 111a, 111b, electronic data sources 120a-d (collectively electronic data sources 120), end-user devices 140a-c (collectively end-user devices 140), an administrator computing device 150, and a medical device 160 having a medical device computer 162. Various components depicted in FIG. 1 may belong to a radiotherapy clinic at which patients may receive radiotherapy treatment, in some cases via one or more radiotherapy machines located within the clinic (e.g., medical device 160). The above-mentioned components may be connected to each other through a network 130. Examples of the network 130 may include, but are not limited to, private or public LAN, WLAN, MAN, WAN, and the Internet. The network 130 may include wired and/or wireless communications according to one or more standards and/or via one or more transport mediums.

The system 100 is not confined to the components described herein and may include additional or other components, not shown for brevity, which are to be considered within the scope of the embodiments described herein.

The communication over the network 130 may be performed in accordance with various communication protocols such as Transmission Control Protocol and Internet Protocol (TCP/IP), User Datagram Protocol (UDP), and IEEE communication protocols. In one example, the network 130 may include wireless communications according to Bluetooth specification sets or another standard or proprietary wireless communication protocol. In another example, the network 130 may also include communications over a cellular network, including, e.g., a GSM (Global System for Mobile Communications), CDMA (Code Division Multiple Access), EDGE (Enhanced Data for Global Evolution) network.

The analytics server 110a may generate and display an electronic platform configured to use various computer models 111 (including artificial intelligence and/or machine learning models such as Discriminator 111a and Generator 111b) for automated localized evaluation of contours. The electronic platform may display one or more medical images such as images of patient organs of interest, and images of contours of such organs. At an inference phase for a patient treatment plan, the electronic platform may display a confidence score indicative of an accuracy of medical images containing contours of a current patient's organs of interest or other target volumes. Depending on confidence score determined, the platform may display regions of medical images containing contours of organs of interest that contribute to a negative classification. These regions may be highlighted and reported for quality assurance review. Disclosed embodiments may provide visual indications of confidence level of localized regions of the contours, e.g., via heat maps.

The electronic platform may include a graphical user interface (GUI) displayed on each electronic data source 120, the end-user devices 140, and/or the administrator computing device 150. An example of the electronic platform generated and hosted by the analytics server 110a may be a web-based application or a website configured to be displayed on different electronic devices, such as mobile devices, tablets, personal computer, and the like.

In a non-limiting example, a physician or radiation oncologist operating the medical professional device 120b, 140c may access the platform, review the confidence score and medical images, and in appropriate cases may initiate a manual quality assurance review. The physician or radiation oncologist may review results highlighting problematic regions of organs of interest that contribute to a low confidence score for an organ contour. The physician or radiation oncologist may visually inspect heat maps or other data visualizations displaying spatial patterns of confidence level of localized regions of the contours. Therefore, the medical professional devices (e.g., the medical professional device 140c) may be used as both a device to display results predicted by the analytics server 110a and in some cases may also be used as an electronic data source (e.g., electronic data source 120b) to train the machine learning models 111.

The analytics server 110a may host a website accessible to users operating any of the electronic devices described herein (e.g., end users, medical professionals), where the content presented via the various webpages may be controlled based upon each particular user's role or viewing permissions. The analytics server 110a may be any computing device comprising a processor and non-transitory machine-readable storage capable of executing the various tasks and processes described herein. The analytics server 110a may employ various processors such as central processing units (CPU) and graphics processing unit (GPU), among others. Non-limiting examples of such computing devices may include workstation computers, laptop computers, server computers, and the like. While the system 100 includes a single analytics server 110a, the analytics server 110a may include any number of computing devices operating in a distributed computing environment, such as a cloud environment.

The analytics server 110*a* may execute software applications configured to display the electronic platform (e.g., host a website), which may generate and serve various webpages to each electronic data source 120 and/or end-user devices 140. Different users may use the website to view and/or interact with displayed content.

The analytics server 110*a* may be configured to require user authentication based upon a set of user authorization credentials (e.g., username, password, biometrics, cryptographic certificate, and the like). The analytics server 110*a* may access the system database 110*b* configured to store user credentials, which the analytics server 110*a* may be configured to reference in order to determine whether a set of entered credentials (purportedly authenticating the user) match an appropriate set of credentials that identify and authenticate the user.

The analytics server 110*a* may generate and host webpages based upon a particular user's role within the system 100. In such implementations, the user's role may be defined by data fields and input fields in user records stored in the system database 110*b*. The analytics server 110*a* may authenticate the user and may identify the user's role by executing an access directory protocol (e.g., LDAP). The analytics server 110*a* may generate webpage content that is customized according to the user's role defined by the user record in the system database 110*b*.

The analytics server 110*a* may receive medical images from a user or retrieve such data from a data repository, analyze the data, and display the results on the electronic platform. For instance, in a non-limiting example, the analytics server 110*a* may query and retrieve medical images from the database 120*d* and combine the medical images with segment data received from a physician operating the medical professional device 120*b*. Additionally, or alternatively, the analytics server 110*a* may segment the medical image automatically or perform other pre-processing steps on the medical image captured from the medical device 160.

The analytics server 110*a* may execute various machine learning models 111 (e.g., Discriminator 111*a* and Generator 111*b*) to analyze the retrieved data. The analytics server 110*a* may then display the results via the electronic platform on the administrator computing device 150 and/or the end-user devices 140.

The electronic data sources 120 may represent various electronic data sources that contain, retrieve, and/or input data associated with a patient's treatment plan including patient data and treatment data. For instance, the analytics server 110*a* may use the clinic computer 120*a*, medical professional device 120*b*, server 120*c* (associated with a physician and/or clinic), and database 120*d* (associated with the physician and/or the clinic) to retrieve/receive data associated with the patient's treatment plan.

End-user devices 140 may be any computing device comprising a processor and a non-transitory machine-readable storage medium capable of performing the various tasks and processes described herein. Non-limiting examples of an end-user device 140 may be a workstation computer, laptop computer, tablet computer, and server computer. In operation, various users may use end-user devices 140 to access the GUI operationally managed by the analytics server 110*a*. Specifically, the end-user devices 140 may include clinic computer 140*a*, clinic server 140*b*, and a medical processional device 140*c*. Even though referred to herein as "end user" devices, these devices may not always be operated by end users. For instance, the clinic server 140*b* may not be directly used by an end user. However, the results stored onto the clinic server 140*b* may be used to populate various GUIs accessed by an end user via the medical professional device 140*c*.

The administrator computing device 150 may represent a computing device operated by a system administrator. The administrator computing device 150 may be configured to display radiation therapy treatment attributes generated by the analytics server 110*a* (e.g., various analytic metrics determined during training of one or more machine learning models and/or systems); monitor various models 111 utilized by the analytics server 110*a*, electronic data sources 120, and/or end-user devices 140; review feedback; and/or facilitate training or retraining (calibration) of the machine learning models 111 that are maintained by the analytics server 110*a*.

The medical device 160 may be a radiotherapy machine configured to implement a patient's radiotherapy treatment. The medical device 160 may also include an imaging device capable of emitting radiation such that the medical device 160 may perform imaging according to various methods to accurately image the internal structure of a patient. For instance, the medical device 160 may include a rotating system (e.g., a static or rotating multi-view system). A non-limiting example of a multi-view system may include a stereo systems (e.g., two systems may be arranged orthogonally). The medical device 160 may also be in communication with a medical device computer 162 that is configured to display various GUIs discussed herein. For instance, the analytics server 110*a* may display the results predicted by the machine learning models 111*a*, 111*b* onto the medical device computer 162.

In operation, a physician or other medical professional may access an application executing on the medical professional device 120*b* and input patient data and the patient's treatment data (e.g., patient information, patient diagnosis, radiation therapy radiation requirements and thresholds). The analytics server 110*a* may then use a patient identifier to query patient data (e.g., patient anatomy and/or medical images) from the electronic data sources 120. The analytics server may then identify a clinic associated with the patient (e.g., clinic performing the treatment) and retrieve one or more files associated with treatment templates and clinic rules. The analytics server 110*a* may then utilize the systems and methods described herein to generate data pertaining to automated localized evaluation of contours.

A medical professional at a radiotherapy clinic may access an end-user device 140 located at the clinic or access an account associated with the clinic. The medical professional may provide an input at a user interface that causes the end user device 140 to transmit a request to access machine learning models 111 that are associated with the clinic and/or the radiotherapy machines located within the clinic. The request may include an identifier associated with the machine learning models 111, the clinic, a treatment plan generated by the one or more medical professionals, and/or the set of radiotherapy machines that the analytics server 110*a* may use as a key in a look-up table to identify the machine learning models 111. The analytics server 110*a* may receive the request and, in some cases, after authenticating the user, identify the machine learning models 111 via the identifier. The analytics server 110*a* may transmit the identified machine learning models 111 to the end-user device 140 or send an alert indicating the end-user device is authorized to access the models 111. Upon receipt or access to the machine learning model 111*s*, the end user device 140 may perform the systems and methods described herein to train or retrain the machine learning models 111 to predict automated localized evaluations of contours.

The analytics server 110a may store machine learning models 111 (e.g., neural networks, random forest, support vector machines, or other deep learning models including Discriminator 111a and Generator 111b, combined in GAN 111), that are trained to predict the anatomical structure represented by various pixels or voxels of a medical image. Various machine learning techniques may involve "training" the machine learning models to predict (e.g., estimate the likelihood of) each pixel or voxel of a medical image being associated with or otherwise representing a particular anatomical structure.

Machine learning models 111 may be stored in the system database 110b and may correspond to individual radiotherapy clinics or otherwise different sets of radiotherapy machines (e.g., radiotherapy machines that are located at individual radiotherapy clinics, are located in different geographical regions, treat specific types of diseases such as different types of cancer, treat specific genders, etc.). For example, the machine learning model 111 may be associated with an identifier indicating the radiotherapy clinic, set of radiotherapy machines, or a specific disease.

In various embodiments, machine learning models 111 use one or more deep learning engines to perform automatic segmentation of image data for radiotherapy treatment planning. Although exemplified using deep convolutional neural networks, it should be understood that any alternative and/or additional deep learning model(s) may be used to implement deep learning engines. The deep learning engines include processing pathways that are trained during training phase. Once trained, deep learning engines may be used (e.g., by a clinician) to perform automatic segmentation for current patients during inference phase.

One type of deep learning engine is a convolutional neural network (CNN). A CNN is a branch of neural networks and consists of a stack of layers each performing a specific operation, e.g., convolution, pooling, loss calculation, etc. Each intermediate layer receives the output of the previous layer as its input. The beginning layer is an input layer, which is directly connected to an input image and may have a number of neurons equal to the number of pixels in the input image. The next set of layers are convolutional layers that present the results of convolving a certain number of filters with the input data and perform as a feature extractor. The filters, commonly known as kernels, are of arbitrary sizes defined by designers. Each neuron responds only to a specific area of the previous layer, called receptive field. The output of each convolution layer is considered as an activation map, which highlights the effect of applying a specific filter on the input. Convolutional layers may be followed by activation layers to apply non-linearity to the outputs of each layer. The next layer can be a pooling layer that helps to reduce the dimensionality of the convolution's output. In various implementations, high-level abstractions are extracted by fully connected layers. The weights of neural connections and the kernels may be continuously optimized in the training phase.

In practice, training data may be user-generated through observations and experience to facilitate supervised learning. For example, training data may be extracted from past treatment plans developed for prior patients. Training data may be pre-processed via any suitable data augmentation approach (e.g., rotation, flipping, translation, scaling, noise addition, cropping, any combination thereof, etc.) to produce a new dataset with modified properties to improve model generalization using ground truth.

As shown in FIG. 1, models 111 for automatic localized evaluation of contours of organs of interest incorporate a Discriminator 111a and a Generator 111b combined in GAN 111. The generator 111b may be CNN such as U-NET configured to generate segmentations. GAN 111 is an adversarial network that serves as a classifier. U-NET 111b generates segmentations during model training, and GAN discriminator 111a evaluates the segmentations. Models 111 may apply GAN to determine weights of interior layers of the discriminator 111a. GAN 111 utilizes unsupervised machine learning based on indirect training through the discriminator, which itself may be updated dynamically. The training of the adversarial network 111 can be based on similar organs or based on image segmentations via different machine learning models.

Inputs to the models 111 include a set of image pairs each of which includes a medical image such as a CT scan and a segmentation or contour. Image pairs may embody a correct association of the CT scan with a mask or segmentation created from the CT scan. Alternatively, image pairs may embody an association of the CT scan with a fake or incorrect mask. GAN discriminator 111a evaluates image pairs to determine which image pairs are correctly matched (e.g., have sufficiently high confidence score), and which image pairs are incorrectly matched. Model outputs may include a confidence score indicating likelihood that the image pair is matched, and may include a binary classification (e.g., Matched or Unmatched).

Figure 2:
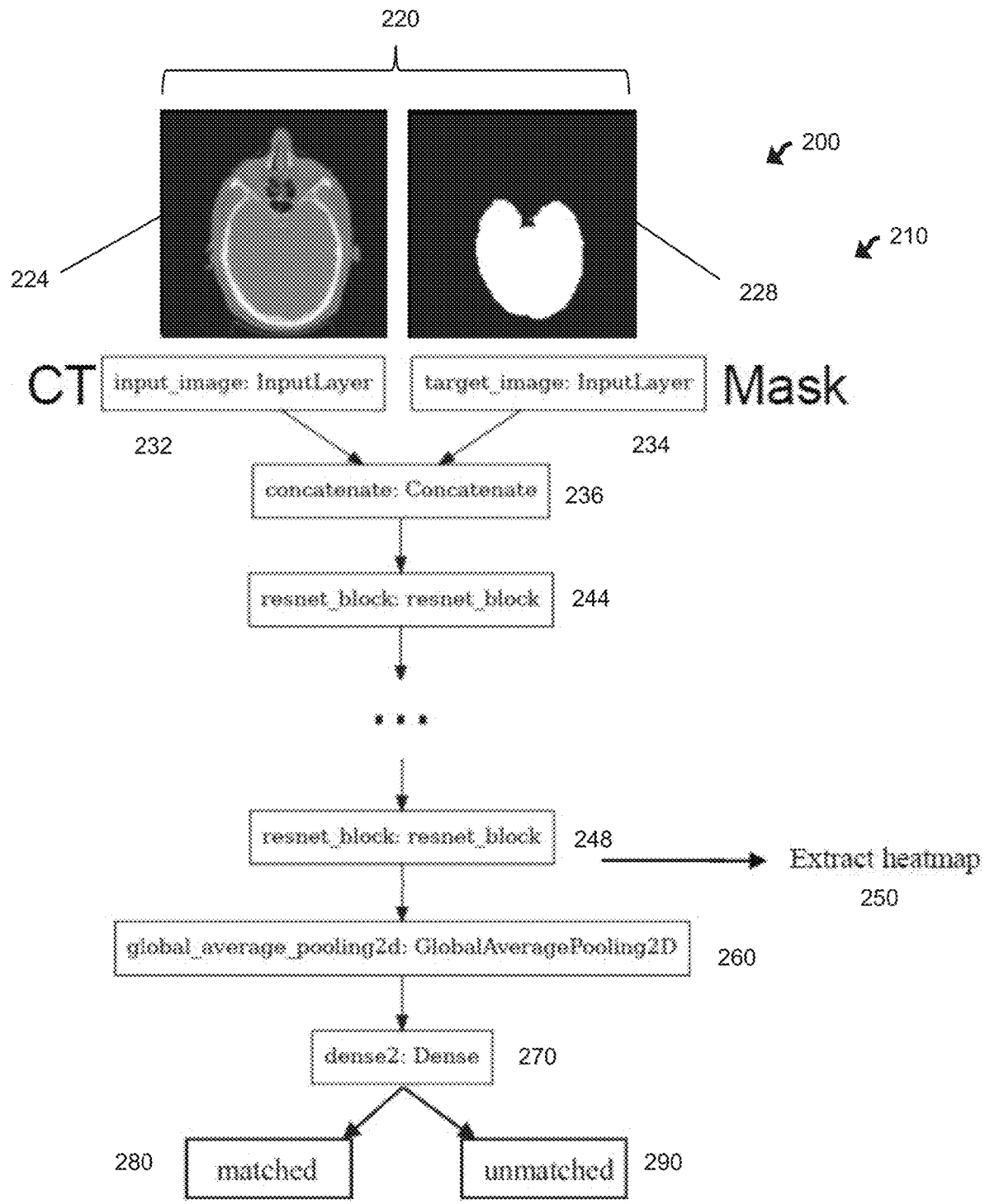
FIG. 2 illustrates a localized evaluation network, according to an embodiment.

The flow chart of FIG. 2 shows a localized evaluation network 200. Localized evaluation network 200 includes a discriminator, which acts as a classifier. The localized evaluation network also includes a generative network, or generator. In an embodiment, the discriminator and generator collectively form a Generative Adversarial Network (GAN). Localized evaluation network 200 may apply the GAN to determine weights of interior layers of the discriminator. In an embodiment, the generative network may be a CNN such as U-Net configured to create segmentations.

Network 200 receives an image pair 220 as input. The image pair includes the medical image on the left (CT 224) and the segmentation or contour on the right (Mask 228). In an embodiment, a clinician has delineated the brain in the Mask 228. The Mask 228 may be produced by autosegmentation, or may be produced by a human such as a radiation therapist or medical dosimetric. Image pair 220 may embody a correct association of CT 224 with a mask 228 created from the CT scan. This type of image pair may be labeled as CORRECT in training data of a supervised training protocol. Alternatively, image pair 220 may embody an association of CT 224 with a fake or incorrect mask 228. This type of image pair may be labeled as INCORRECT in training data of a supervised training protocol. For example, an incorrect mask may be selected from a series of segmentations different than the mask correctly associated with CT 224.

Input layer 236 concatenates the CT image input 232 and the Mask image input, also called target image, 234. This results in an N×N×2 spatially local pattern for each convolutional layer, including two values for each pixel. Each of a series of ResNet blocks 244 . . . 248 of the network corresponds to a given convolutional layer. Using residual blocks 244 . . . 248, in addition to feeding the layer activation to the next layer, the activation map is fast-forwarded to a deeper layer in the convolutional neural network. Each layer may feed into the next layer and may directly feed into layers about 2-3 hops away. ResNets allow neural networks with large number of layers to be trained more easily.

Each convolutional layer takes a small portion of the image and applies convolutional filters to it in order to abstract features of the image. ResNet block layers 244 . . . 248 apply convolutional filters to the image to abstract the image to a feature map, also called an activation map. Each filter may be replicated across the entire visual field. These replicated units share the same parameterization (weight vector and bias) and form an activation map. The convolutional filters identify features present in the image such as edges, vertical lines, horizontal lines, bends, etc. Given convolutional filters may correspond to given spatial patterns, such as a filter that looks for horizontal lines or a filter that looks for vertical lines. Convolutional filters have learnable parameters. The weights of a layer are the values determined by applying the convolutional filters to the layer.

Just before the final output layer, the CNN performs global average pooling 260. The features thus obtained are fed to a dense layer 270 that produces the desired output. Dense layer 270 is a fully connected layer in which all the neurons in the layer are connected to those in the next layer. In the localized evaluation network 200, dense layer 270 outputs a single number representing a binary classification, either Matched 280 or Unmatched 290. Dense 270 may output a confidence score S, e.g., a value between 0 and 1 that may classify the image pair 220 as Matched 280 if S>0.5 and may classify the image pair 220 as Unmatched 290 if S≤0.5.

The confidence scores of respective localized regions may correspond to weights of layers of the machine learning model. The weights of model layers represent contributions to the final confidence score. For example, layer weights may indicate image regions that make a major contribution to an Unmatched 290 binary classification. These regions may represent the highest priority for quality assurance review of a low confidence score segmentation.

In disclosed embodiments, the network 200 applies Class Activation Maps (CAM) as a visualization technique. A CAM for a particular target category indicates the discriminative region used by CNN to identify the category. In an embodiment, a CAM looks at the intermediate layers before arriving at the final result. CAM examines each layer and evaluates how much each sub-image or image region contributes to the binary classification 280, 290. The discriminator may generate a CAM to determine image regions that result in a reduced confidence score based on training data from the set of third images and the set of fourth images.

Disclosed embodiments may apply various techniques to visualize local features of an image captured in activation maps. Visualization techniques may generate a heat map. In disclosed embodiments, a heat map, also referred to herein as spatial heat map, employs variation in color such as by intensity or hue to provide obvious visual cues about how a target phenomenon varies over space. A spatial heat map may be created by a software program for visualizing spatial data.

In an embodiment, localized evaluation network 200 applies Gradient-weighted Class Activation Mapping (Grad-CAM) to provide visual explanations of local features of an image. Grad-CAM is described in Ramprasaath R. Selvaraju, Michael Cogswell, Abhishek Das, Ramakrishna Vedantam, Devi Parikh, Dhruv Batra; "Grad-CAM: Visual Explanations from Deep Networks via Gradient-based Localization," 2017 IEEE International Conference on Computer Vision. Grad-CAM uses gradients of a target concept entering the final convolutional layer to produce a coarse localization map. Grad-CAM highlights important regions in the image for predicting the target concept. Grad-CAM creates a high-resolution class-discriminative visualization. Disclosed embodiments apply Grad-CAM to understand how local image features affect an overall confidence score for the image. In an embodiment, Grad-CAM computes a coarse Grad-CAM localization to generate a heat map. The heat map may show relative contributions of different local regions to a confidence score.

Figure 3:
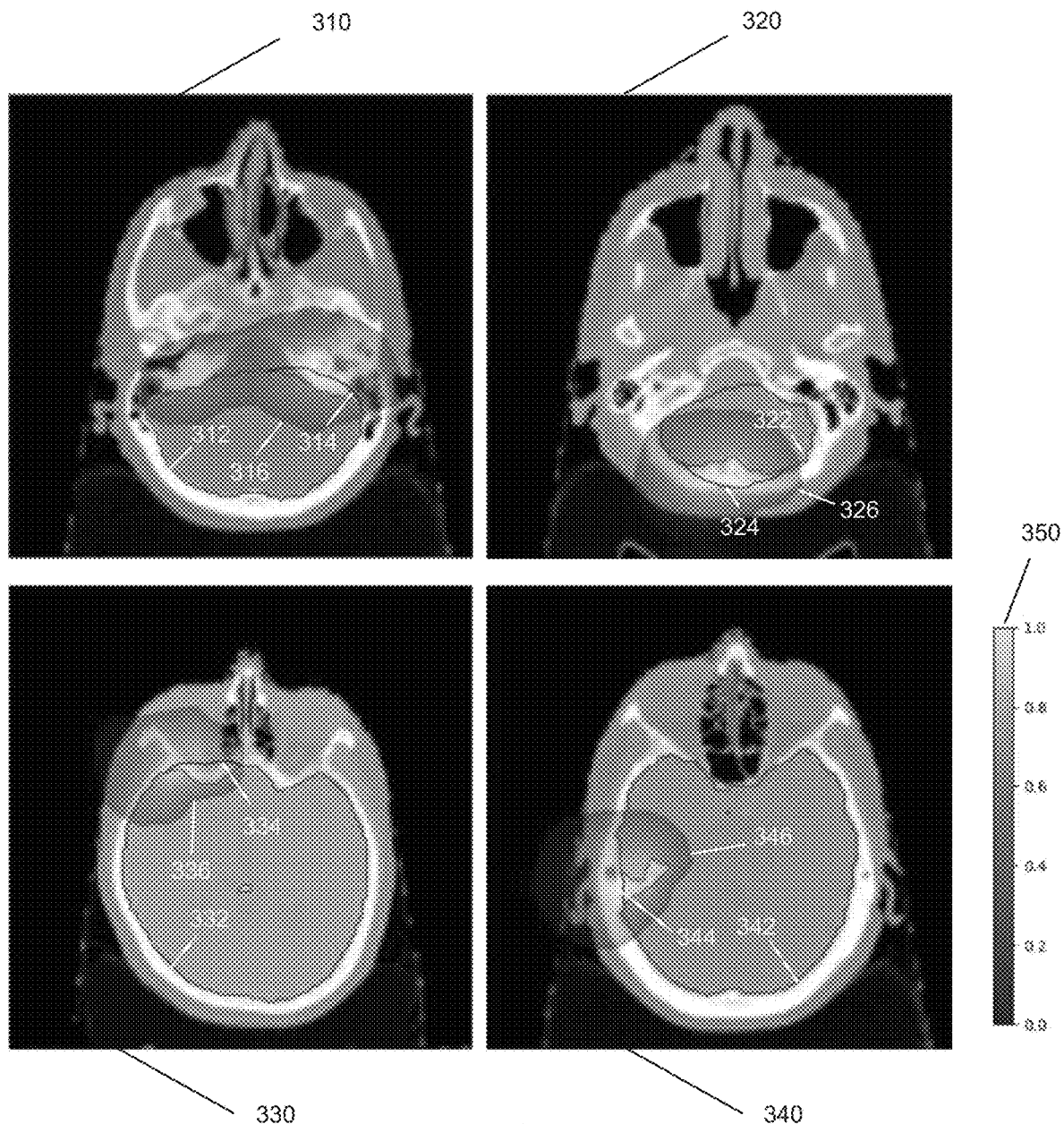
FIG. 3 illustrates results from running the trained adversarial network discriminator to create localized evaluation visualizations, according to an embodiment.

FIG. 3 illustrates results from running the trained adversarial network discriminator of FIG. 2 at inference time to generate a series of medical image/mask pairs 310, 320, 330, and 340. Training data for the adversarial network discriminator inputted four medical images from reference: Martin Vallières, Emily Kay-Rivest, Léo Jean Perrin, Xavier Liem, Christophe Furstoss, Nader Khaouam, Phuc Félix Nguyen-Tan, Chang-Shu Wang, Khalil Sultanem, "Data from Head-Neck-PET-CT," The Cancer Imaging Archive, doi: 10.7937/K9/TCIA.2017.8oje5q00 (2017).

In each medical image/mask pair, a main black-and-white image shows a CT slice of the brain. Each of the green lines 312, 322, 332, and 342 contours the inside of the skull and represents the ground truth segmentation. For example, the ground truth segmentation may be delineated by a human, or may be an autosegmentation evaluated to be correct by human review. Each of the black lines 314, 324, 334, and 344 contours the inside of the skull and represents an incorrect segmentation.

The trained adversarial network generated heat maps 316, 326, 336, and 346 providing CAM visualizations. Each color wash includes a heat map having a spatial pattern of hues representing weights of layers of the machine learning model captured in the CAM. The weights of layers of the machine learning model may correspond to contributions of localized regions of the segmentation to an overall confidence score. As shown in the color gradient bar 350, higher values corresponding to yellow and green hues represent layer regions that more likely to be incorrect. Lower values corresponding to blue and purple hues represent layer regions that are more likely to be correct. The yellow and green regions provide the highest contributions to a negative overall confidence score.

FIG. 4 illustrates a flow diagram of a process executed by an analytic server. In step 402, the analytic server executes a machine learning model that receives an input of a first image of an anatomical region of a patient depicting an organ. A second image includes an overlay contouring an outline of the anatomical region. The machine learning model is configured to predict a first confidence score indicating a likelihood of the overlay correctly contouring the outline. The machine learning model is trained based on a set of third images depicting a set of second organs having a set of second outlines and a set of fourth images including a set of second overlays incorrectly contouring the set of second outlines.

In various embodiments of step 402, the machine learning model is further trained based on a set of fifth images depicting a set of third organs having a set of third outlines and a set of sixth images including a set of fourth overlays correctly contouring the set of third outlines.

In step 404, the analytic server presents, for display on a graphical user interface, the first image and a third overlay. A plurality of localized regions within the third overlay have a visual attribute that represents contributions of respective localized regions of the plurality of localized regions to the first confidence score.

The various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of this disclosure or the claims.

Embodiments implemented in computer software may be implemented in software, firmware, middleware, microcode, hardware description languages, or any combination thereof. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

The actual software code or specialized control hardware used to implement these systems and methods is not limiting of the claimed features or this disclosure. Thus, the operation and behavior of the systems and methods were described without reference to the specific software code being understood that software and control hardware can be designed to implement the systems and methods based on the description herein.

When implemented in software, the functions may be stored as one or more instructions or code on a non-transitory computer-readable or processor-readable storage medium. The steps of a method or algorithm disclosed herein may be embodied in a processor-executable software module, which may reside on a computer-readable or processor-readable storage medium. A non-transitory computer-readable or processor-readable media includes both computer storage media and tangible storage media that facilitate transfer of a computer program from one place to another. A non-transitory processor-readable storage media may be any available media that may be accessed by a computer. By way of example, and not limitation, such non-transitory processor-readable media may comprise RAM, ROM, EEPROM, CD-ROM or other optical disk storage, magnetic disk storage or other magnetic storage devices, or any other tangible storage medium that may be used to store desired program code in the form of instructions or data structures and that may be accessed by a computer or processor. Disk and disc, as used herein, include compact disc (CD), laser disc, optical disc, digital versatile disc (DVD), floppy disk, and Blu-ray disc where disks usually reproduce data magnetically, while discs reproduce data optically with lasers. Combinations of the above should also be included within the scope of computer-readable media. Additionally, the operations of a method or algorithm may reside as one or any combination or set of codes and/or instructions on a non-transitory processor-readable medium and/or computer-readable medium, which may be incorporated into a computer program product.

The preceding description of the disclosed embodiments is provided to enable any person skilled in the art to make or use the embodiments described herein and variations thereof. Various modifications to these embodiments will be readily apparent to those skilled in the art, and the principles defined herein may be applied to other embodiments without departing from the spirit or scope of the subject matter disclosed herein. Thus, the present disclosure is not intended to be limited to the embodiments shown herein but is to be accorded the widest scope consistent with the following claims and the principles and novel features disclosed herein.

While various aspects and embodiments have been disclosed, other aspects and embodiments are contemplated. The various aspects and embodiments disclosed are for purposes of illustration and are not intended to be limiting, with the true scope and spirit being indicated by the following claims.

What we claim is:

1. A method comprising:
   executing, by a processor, a machine learning model that receives an input of a first image of an anatomical region of a patient depicting an organ having an outline and a second image comprising an overlay contouring the outline and further configured to predict a first confidence score indicating a likelihood of the overlay correctly contouring the outline,
   wherein the machine learning model is trained based on a set of third images depicting a set of second organs having a set of second outlines and a set of fourth images comprising a set of second overlays incorrectly contouring the set of second outlines; and
   presenting, by the processor for display on a graphical user interface, the first image and a third overlay, wherein a plurality of localized regions within the third overlay has a visual attribute that represents contributions of respective localized regions of the plurality of localized regions to the first confidence score, the visual attribute visually distinguishing areas of the first image in accordance with the likelihood of the overlay contouring being correct, wherein the visual attribute comprises a hue that corresponds to at least one weight of at least one layer of the machine learning model.

2. The method of claim 1, wherein the set of fourth images comprising the set of second overlays is generated via a second machine learning model.

3. The method of claim 2, wherein the set of fourth images comprising the set of second overlays were previously generated via the second machine learning model.

4. The method of claim 1, wherein the machine learning model is further trained based on a set of fifth images depicting a set of third organs having a set of third outlines and a set of sixth images comprising a set of fourth overlays correctly contouring the set of third outlines.

5. The method of claim 1, wherein the first confidence score indicates a likelihood of the plurality of localized regions of the overlay correctly contouring localized regions of the outline.

6. The method of claim 1, wherein the machine learning model is trained by applying a generative adversarial network (GAN) to training data from the set of third images and the set of fourth images.

7. The method of claim 6, wherein the machine learning model is configured to apply the GAN to determine weights of interior layers of a discriminator.

8. The method of claim 7, wherein the discriminator generates a Class Activation Map (CAM) to determine image regions that result in a reduced confidence score based on training data from the set of third images and the set of fourth images.

9. The method of claim 1, wherein the contributions of the respective localized regions to the first confidence score correspond to weights of layers of the machine learning model.

10. The method of claim 1, wherein the visual attribute corresponds to color coding of a spatial heat map.

11. The method of claim 1, wherein the machine learning model is a binary classifier with matched and unmatched classes.

12. The method of claim 1, wherein the first image is a computed tomography (CT) image, magnetic resonance imaging (MRI) image, or positron emission tomography (PET) scan image.

13. A method comprising:
   executing, by a processor, a machine learning model that receives an input of a first image of an anatomical region of a patient depicting an organ having an outline and a second image comprising an overlay contouring the outline and further configured to predict a first confidence score indicating a likelihood of the overlay correctly contouring the outline,
      wherein the machine learning model is trained based on a set of third images depicting a set of second organs having a set of second outlines and a set of fourth images comprising a set of second overlays incorrectly contouring the set of second outlines, wherein the machine learning model is further trained based on a set of fifth images depicting a set of third organs having a set of third outlines and a set of sixth images comprising a set of fourth overlays correctly contouring the set of third outlines; and
   presenting, by the processor for display on a graphical user interface, the first image and a third overlay, wherein a plurality of localized regions within the third overlay has a visual attribute that represents contributions of respective localized regions of the plurality of localized regions to the first confidence score, the visual attribute visually distinguishing areas of the first image in accordance with the likelihood of the overlay contouring being correct, wherein the visual attribute comprises a hue that corresponds to at least one weight of at least one layer of the machine learning model.

14. A system comprising:
   a server comprising a processor and a non-transitory computer-readable medium containing instructions that when executed by the processor causes the processor to perform operations comprising:
      executing a machine learning model that receives an input of a first image of an anatomical region of a patient depicting an organ having an outline and a second image comprising an overlay contouring the outline and further configured to predict a first confidence score indicating a likelihood of the overlay correctly contouring n the outline, wherein the machine learning model is trained based on a set of third images depicting a set of second organs having a set of second outlines and a set of fourth images comprising a set of second overlays incorrectly contouring the set of second outlines; and
      present, for display on a graphical user interface, the first image and a third overlay where each of a plurality of localized regions within the third overlay, wherein a plurality of localized regions within the third overlay have a visual attribute that represents contributions of respective localized regions of the plurality of localized regions to the first confidence score, the visual attribute visually distinguishing areas of the first image in accordance with the likelihood of the overlay contouring being correct, wherein the visual attribute comprises a hue that corresponds to at least one weight of at least one layer of the machine learning model.

15. The system of claim 14, wherein the non-transitory computer-readable medium contains instructions that when executed by the processor causes the processor to train the machine learning model by applying a generative adversarial network (GAN) to training data from the set of third images and the set of fourth images.

16. The system of claim 15, wherein the machine learning model is configured to apply the GAN to determine weights of interior layers of a discriminator.

17. The system of claim 16, wherein the discriminator generates a Class Activation Map (CAM) to determine image regions that result in a reduced confidence score based on training data from the set of third images and the set of fourth images.

18. The system of claim 17, wherein the CAM comprises a Gradient-weighted Class Activation Map (Grad-CAM).

19. The system of claim 14, wherein the visual attribute corresponds to color coding of a spatial heat map.

20. The system of claim 14, wherein the machine learning model is further trained based on a set of fifth images depicting a set of third organs having a set of third outlines and a set of sixth images comprising a set of fourth overlays correctly contouring the set of third outlines.

* * * * *